United States Patent [19]

Boustta et al.

[11] Patent Number: 5,026,821

[45] Date of Patent: Jun. 25, 1991

[54] POLYMERS OF CITRIC ACID AND DIAMINES, A PROCESS FOR THEIR PREPARATION AND THEIR USES, IN PARTICULAR AS CARRIERS OF DRUG

[75] Inventors: Mahfoud Boustta, Rouen; Jovanka Huquet, St. Martin Boscherville; Michel Vert, Mont Saint Aignan, all of France

[73] Assignee: Sanofi, Paris, France

[21] Appl. No.: 318,032

[22] Filed: Mar. 2, 1989

[30] Foreign Application Priority Data

Mar. 8, 1988 [FR] France ................................ 88 02956

[51] Int. Cl.$^5$ ....................... C08G 69/26; C07C 59/08
[52] U.S. Cl. .................................. 528/350; 528/341; 528/342; 562/589
[58] Field of Search ....................... 528/341, 350, 342; 562/589

[56] References Cited

U.S. PATENT DOCUMENTS 1,016,833  9/1962  Anderson ............................ 528/341
4,064,086 12/1977  Cowsar et al. ..................... 528/341
4,873,311 10/1989  Bornack, Jr. et al. ............. 528/350

OTHER PUBLICATIONS

J. Polymeric Science Part A-1 5, p. 2441, 1967 by Ogata, N.
J. Polymeric Science 13, p. 1793 (1975).
J. Polymeric Science Part A-1 9, p. 2413 (1971).
Makromol. Chemical 186, p. 939 (1985).

Primary Examiner—Morton Foelak
Assistant Examiner—Kathryne E. Shelborne
Attorney, Agent, or Firm—Wegner, Cantor Mueller & Player

[57] ABSTRACT

The present invention provides polyamides produced by the condensation of diamines with citric acid through the carboxyl groups attached to the carbon atoms in positions 1 and 3.

These polyamides can be used for the preparation of controlled-release forms of drugs.

23 Claims, No Drawings

POLYMERS OF CITRIC ACID AND DIAMINES, A PROCESS FOR THEIR PREPARATION AND THEIR USES, IN PARTICULAR AS CARRIERS OF DRUG

The present invention relates to hydrophylic polymers composed of polyamides resulting from the condensation of citric acid with diamines through the intermediary of the carboxyl groups attached to the carbon atoms in positions 1 and 3, i.e. in position beta to the hydroxyl group, as well as a process for their preparation and the application of these biodegradable polymers as carriers or as reservoirs of drugs to obtain the controlled progressive release of these latter in the organism, as sutures or ligatures or as surgical prostheses for the substitution and strengthening of vascular tissues, ligaments and damaged bones and as surgical adhesives.

Polyamides with hydrophilic functions have already been described. Those prepared by condensation of L-tartaric acid with hexamethylene diamine described by Minoura et al. in J. Polym. Sc. Part A-1 5 p. 2441 (1967) and by N. Ogata et al. in J. Polym. Sc. 13 p. 1793 (1975) may be mentioned; the former are soluble in water but of low molecular weight whereas the latter are insoluble in water. Water-soluble polyamides derived from L-lysine and aliphatic or aromatic diacids have also been prepared by interfacial polycondensation as mentioned in Makromol. Chem. 109 p. 239 (1967) and J. Polym. Sc. Part A-1 9 p. 2413 (1971) or by polycondensation in solution as mentioned in Makromol. Chem. 186 p. 939 (1985).

Nevertheless, polyamides derived from citric acid have never been described; however, the presence in this monomer having three carboxylic acid groups and a hydroxyl group make it possible to prepare a polymer having at least 2 hydrophilic functions, which would confer to it a certain solubility in water, whatever the pH of the medium and in polar solvents, whereas the presence of a carboxyl group free or blocked in a labile intramolecular bond would confer high reactivity to the polymer, which could be made use of to bind various molecules, for example, drugs to the backbone of the linear polymer by ionic or covalent bonds or to crosslink it if it is considered desirable to reduce its intrinsic solubility and increase its mechanical resistance.

The polymers of the invention are represented in particular by the following structural formula:

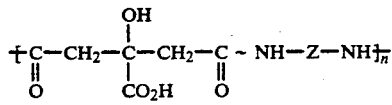

in which n is an integer less than 1000, and lies preferably between 20 and 300, and Z is selected from a linear or branched aliphatic chain having from 2 to 10 carbon atoms, and preferably from 2 to 8 carbon atoms, and which may include hydrophilic groups such as OH and COOH, or in which oxygen or sulfur atoms may be intercalated, or Z is selected from an aryl chain such as $-C_6H_4-$, or an alkylaryl chain such as $-CH_2-C_6H_4-CH_2$ or $-CH_2-C_6H_4-$, and ~ represents the two types of linkage when Z is asymmetric.

In fact, in this case, the polymers is constituted of two types of units resulting from the condensation of one or other amine groups of the diamine with the free carboxyl group of the growing polymer.

In order to be useful in therapy, in particular for controlled-release forms of drugs, the polymers must preferably be biodegradable and give rise on degradation to molecules which are non-toxic for the organism and easily eliminated; it is know that aliphatic linear polyamides such as nylon ® are relatively insensitive to hydrolysis in vivo; on the other hand, as they are hydrophilic and water-soluble, the polycitramides of the invention are hydrolyzed without difficulty in vivo, even in the absence of proteases, and release citric acid, a metabolite of the Krebs cycle, which is degrated and eliminated by natural metabolic pathways without risk of accumulation or formation of toxic products. When the diamine monomer is a molecule naturally present in the organism of living mammals, all of the products of biodegradation are removed from the organism by natural metabolic pathways and it may be said that the polymer is bioresorbable.

The diamines involved in the preparation of the polymers of the invention can be simple aliphatic or aromatic diamines, preferably symmetrical, such as ethylene-diamine, hexamethylene-diamine, 3,6-dioxa-1,8-octyldiamine, cystamine or the phenylenediamines.

The diamines may also comprise other free hydrophilic groups, for example hydroxyl or carboxylic groups, as in diaminopimelic acid, in this case, the group capable of reaction during polycondensation must be protected prior to the polymerization.

Especially when the polymers of the invention are intended for pharmaceutical applications, the diamines naturally present in the organism such as cystamine, L-ornithine, L-cystine and, in particular L-lysine are preferred; the dextro-rotatory stereoisomers of these amines or their racemic mixture can also be used.

The copolymers resulting from the polycondensation of citric acid with at least two different diamines are also included in the invention.

A preferred subject of the invention is the polymer resulting from the condensation of citric acid, in which the hydroxyl and carboxylic acid residues attached to the central carbon atom have been appropriately protected for the polymerization by condensation, with L-lysine, the carboxylic acid of which has been appropriately protected for polymerization.

The polymers thus obtained, after the protecting groups have been removed, are hydrophilic and are soluble to varying extents, depending on their molecular weight, in water and solvents miscible with water such as polar aprotic organic solvents and hydroxylated solvents; their solubility in alcohols is particularly useful for the preparation of pharmaceutical forms and it should be noted that most of the polymers resulting from the condensation of alpha amino acids, the utilization of which as biodegradable polymers is a subject of current active interest, are usually soluble only in solvents rarely used in the pharmaceutical industry.

The preferred polymers of the invention are not toxic and are degraded in vivo by hydrolysis which may or may not involve an enzyme, releasing non-toxic substances naturally present in the organism, namely citric acid and L-lysine.

Another subject of the invention is the process for the preparation of these polycitramides. It consists essentially in carrying out polycondensation between a diamine and citric acid, the OH and COOH groups of which attached to the carbon atom in position 2 are blocked and in removing the protecting groups.

The blockage of the OH and COOH groups attached to the carbon atom in position 2 must be selective, i.e. the other COOH groups of citric acid must remain free; in addition, the blocked groups must possess a high degree of stability in the conditions of the polycondensation reaction but must be capable of being deblocked after polymerization without degradation of the polyamide backbone.

It is preferable to protect the OH and COOH groups simultaneously by preparing a derivative of the 1,3-dioxolan-4-one type having the structural formula d by the reaction of an aldehyde with citric acid according to the reaction scheme:

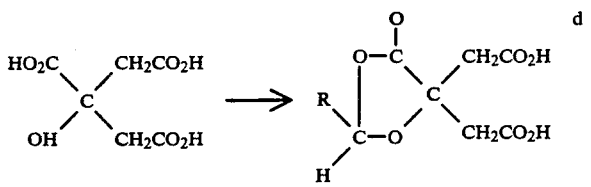

The products of the condensation reaction of citric acid with formaldehyde (R=H), with an aliphatic aldehyde (R=$C_1$-$C_4$ alkyl), with trichloroacetaldehyde (R=$CCl_3$) and with benzaldehyde (R=$C_6H_5$) are known compounds, and it is known that they can be hydrolyzed in either acidic or basic medium to regenerate the citric acid precursor.

It has now been found that citric acid groups can also be regenerated by catalytic hydrogenation of the dioxolanes of formula d and this makes it possible to deblock simultaneously the citric acid and diamine units when the latter have certain reactive functions which have required blockage.

In order to carry out the condensation reaction leading to polymer formation, it is necessary to activate the acid and/or amine groups. It is possible to introduce into an organic solution of the diacid and the diamine a coupling reagent such as dicyclohexylcarbodiimide or N, N'-carbonyl-diimidazole, but prior activation of the acids in the form of acid chloride in a known manner is preferred: for that purpose, the blocked citric acid is reacted with thionyl chloride in excess in the presence or absence of a solvent. Prior activation of the amine groups is also possible by substitution with the trimethylsilyl group or by any other standard reagent. Other coupling reagents such as those used in peptide synthesis can also be advantageously used for the polycondensation reaction.

The polymerization can be carried out in a known manner in solution or by interfacial polycondensation, this latter method being applicable in the case of very reactive substances, such as the acid chlorides, preferably at a temperature close to ambient temperature or even below.

The persons skilled in the art will be able to choose the conditions of polymerization best suited to the preparation of polymers having specific characteristics of molecular weight by referring in particular to the methods known for the preparation of polyamides, and by taking into account the instability of the dioxolane group protecting the citric acid, in basic aqueous medium. The polycondensation of the diacid chloride with a diamine is carried out in a known manner in the presence of a soluble base which will take up the hydrochloric acid liberated; in the case of polymerization in solution, a tertiary amine is usually introduced such as triethylamine or pyridine, whereas in the case of interfacial polymerization a water-soluble carbonate of alkali metal is used.

The process for deblocking the groups which have been protected before the polycondensation depends on the method of protection selected. If the citric acid has been blocked in the form of a dioxolane of formula d, the OH and COOH groups can be regenerated by the action in aqueous or aqueous alcoholic medium of an acid or a base at ambient temperature without degradation of the polyamide backbone.

In the case in which the diamine has reactive groups other than the two $NH_2$ groups implicated in the condensation reaction, the process of the invention will include an additional step for the protection of these groups before polycondensation as well as a step for the deblocking of these blocked groups present in the polymer; this latter may be carried out simultaneously with that for the deblocking of the OH and COOH of the citric acid unit in the polymer. It is obviously necessary that the blocking groups are splitted without degradation of the backbone of the polymer and it is possible, for example, to block the hydroxyl groups of the diamine in the form of esters or carbonates and the carboxylic acid groups in the form of benzyl esters; this latter blocked group is preferred since it makes it possible to regenerate the acid by catalytic hydrogenation or by hydrolysis under mild conditions whereas the esters of linear aliphatic alcohols are hydrolyzed only in strongly acidic or basic media when the polyamide chain would be degraded, at least partially.

It has been observed that the product obtained by interfacial polycondensation of the dichloride of citric acid, protected in the form of a dioxolane of formula d, with a diamine is not composed only of the expected units, i.e. those represented by formulae II$_a$ and II$_b$ if lysine is taken as the example of the diamine, the acidic group of which is protected in the form of a benzyl ester:

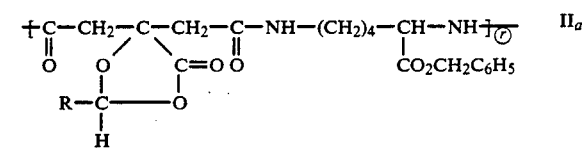

and

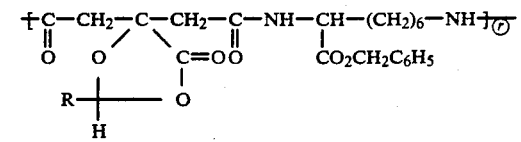

corresponding to 2 possible types of linkage of this asymmetrical diamine, formulae which can also be expressed in the condensed form:

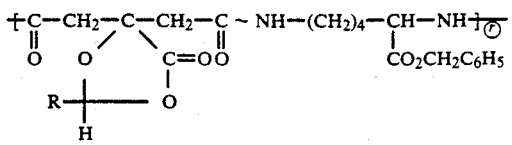

but also included units having cyclic imide groups resulting from an intramolecular side reaction of the dioxolane group such that the raw polycondensate corresponds to the condensed formula III:

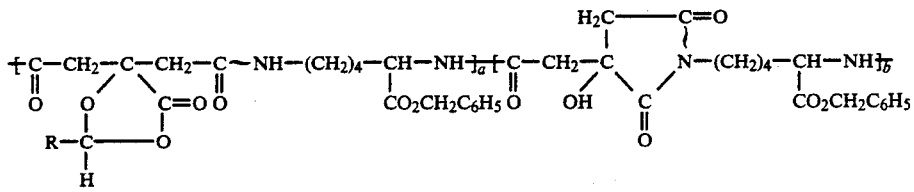

in which a and b are integers, and the ~ expresses the various possibilities for linkage owing to the asymmetry of the precursor.

The proportion of units with imide groups depends on the nature of the R substituent of the dioxolane and on the conditions of the polycondensation, in particular the solvent.

The copolymers of formula III are a subject of the invention; they can be used as biodegradable polymers or as intermediates in the synthesis of polymers of formulae IV and V.

Catalytic hydrogenation of the polymer of formula III liberates the carboxylic acid groups from their benzyl esters and the hydroxyl and carboxylic acid groups included in the dioxolane ring, and a polymer of condensed formula IV is then obtained:

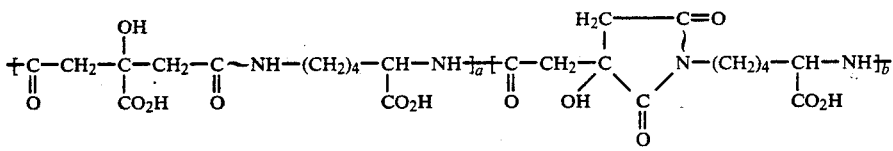

in which a and b are integers.

The hydrogenolysis of the ester groups to give the polymer IV is sometimes difficult to take to completion and, if necessary, the ester groups remaining after hydrogenolysis may be hydrolyzed by reaction with an acid solution such as a solution of hydrochloric acid in a mixture of dimethylformamide and water.

Another subject of the invention is constituted by the copolymer of formula IV as well as by analogous polymers of formula IVa, prepared from diamines other than lysine:

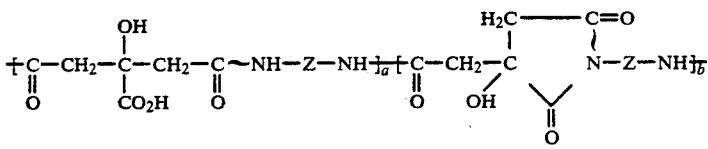

By reaction with a base in aqueous medium, the cyclic imide group of the polymers is opened by cleavage of one or other of the nitrogen-carbonyl bonds to give rise, after acidification, to linear copolymers containing 2 different types of non-cyclic units which are randomly distributed and correspond to the formula V:

$A_p\text{-}B_q$ in which A represents:

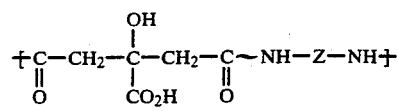

and B represents:

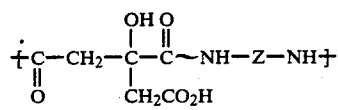

Z having the same meaning as before and p and q represent integers and are such that $p+q=a+b$ and $p>a$ and ~ has the same meaning as before.

The compounds of formula V are another subject of the invention.

In the case in which the polymers of the invention are prepared from a symmetrical diamine, products of more regular structure are obtained, corresponding to formula I in which ~ is —, because there are no longer isomers due to head-to-head and head-to-tail linkages.

Finally, another subject of the invention is the use of the biodegradable, and in some cases bioresorbable polycitramides of formula I, III, IV and V as well as their salts with pharmaceutically acceptable bases, as reservoirs or carriers of drugs in controlled or prolonged release pharmaceutical forms, as sutures or ligatures in surgery, as surgical prostheses, or as adhesives.

Active ingredients can be bound by covalent or ionic linkage to the polymers of the invention to give rise to macromolecular prodrugs or may be intimately mixed with the polymer by known processes or absorbed onto the polymer which may have the form of beads, foils, rods or microporous elements or also be incorporated into aggregate systems of the polymer such as macromolecular microemulsions; they can also be coated by the polymer in particular to form capsules or microcapsules prepared according to known techniques.

Drugs designed to cure or prevent disease or which modify certain biological functions can be formulated in a known manner with the polymers of the invention.

The pharmaceutical forms can be adapted to the mode of administration of the drug, whether by the oral or nasal route, by intravenous or intramuscular injection or by subcutaneous implantation.

The polymers according to the invention are not toxic since, when injected into the mouse by the intraperitoneal or intramuscular route at 700 mg/kg and into the rat by intravenous route at 250 mg/kg, they did not cause death or any apparent sign of toxicity.

Moreover, when implanted by the subcutaneous route into the flank of rats, the local tolerance of the products is excellent in spite, sometimes, of a very mild fibrous reaction.

Examples of the implementation of the invention are described in what follows:

EXAMPLE 1

Interfacial polycondensation of citrobenzal dichloride and L-lysine benzyl ester (a) L-lysine benzyl ester di-p-toluene sulfonic acid salt 30 g of L-lysine ($20.5 \cdot 10^{-2}$ mole) and 70 ml of distilled benzyl alcohol ($67.6 \cdot 10^{-2}$ mole) are introduced into an extractor of the Dean-Stark type; 88.5 g of paratoluene sulfonic acid monohydrate ($46.5 \cdot 10^{-2}$ mole) and 300 ml of benzene are added. The mixture is heated at reflux until all of the water formed in the reaction has been removed. The solution is transferred to a beaker to which 100 ml of methanol are added. The salt is precipitated by the addition of 500 ml of ethyl ether at room temperature. The precipitate is taken up by warming in 300 ml of methanol and reprecipitated by ethyl ether. 100 g of the N,N'-ditosylate of L-lysine benzyl ester are recovered; yield = 84%, M.P. = 163° C.

(b) Citrobenzal (compound of formula d, $R = C_6H_5$)

78 g of citric acid (0.41 mole) and 90 g of benzaldehyde are introduced into a three-necked flask equipped with a mechanical stirrer. The mixture is heated to about 50° C. and 42.5 g of $P_2O_5$ are added in small portions so as to maintain the temperature between 75° and 80° C. The phosphoric anhydride turns red and then black on contact with the mixture. At the end of the addition, the mixture has turned black. Stirring is continued for 90 minutes at a temperature of about 80° C. At the end of the reaction, the black oil is poured while still hot into a mortar containing crushed ice; it solidifies on contact with the ice. The mixture is ground as it is brought to pH 8 by the addition of 4N KOH. The excess benzaldehyde is extracted by means of ethyl acetate. The black aqueous solution is cooled to 0° C. and acidified with concentrated HCl. The citrobenzal separates at the bottom of the flask in the form of an oil. It is extracted with ethyl ether. The ethereal solution is washed with water until the pH becomes neutral, dried over anhydrous $MgSO_4$ and evaporated. About 70 g of white solid are obtained which are dissolved in 300 ml of ethyl acetate by warming. After the yellow solution has been cooled 150 ml of petroleum ether are added which leads to the precipitation of the citrobenzal as white crystals. 51.5 g of crystals are recovered; yield = 45%.

M.p. = 185° C. ($CH_3COOC_2H_5$/petroleum ether). The IR and NMR spectra comply.

(c) Citrobenzal dichloride 14 g of the diacid obtained according to (b) and 40 ml of $SOCl_2$ (distilled beforehand from triphenylphosphite) are heated in a flask fitted with a condenser and a calcium chloride guard tube. The reaction mixture is stirred and heated to reflux until the diacid has completely dissolved (about 2 hours). Reflux is then continued for 15 minutes. At the end of the reaction, the excess thionyl chloride is removed under reduced pressure. 30 ml of benzene or toluene are added to the residue; the mixture is filtered. The solution is heated in the presence of vegetable charcoal, then filtered and evaporated to dryness.

The residue is dissolved in 20 ml of benzene and reprecipitated by petroleum ether. 9,4 g of citrobenzal dichloride are obtained in the form of white needles. Yield: about 60%.

M.p. = 82° C. (toluene/n-hexane).

This compound is readily hydrolyzed by water and is spontaneously converted to the cyclic anhydride; therefore, it should be prepared just before use.

(d) Polycondensation 7.6 g of the N,N-ditosylate of L-lysine benzyl ester ($13.02 \cdot 10^{-3}$ mole), 7.45 g of sodium carbonate decahydrate ($26.04 \cdot 10^{-3}$ mole), necessary to neutralize the acid groups set free and 0.5 g of sodium dodecylsulfate (MERCK) (10% by weight of the diacid chloride) are dissolved in a water-benzene mixture (60 cm$^3$, V/V, 66/33) with vigorous stirring in a laboratory mixer.

With vigorous stirring, (12 to 15000 revs per minute), 4.54 g of citrobenzal dichloride ($14.32 \cdot 10^{-3}$ mole) dissolved is 40 ml of water are added simultaneously in a manner such that 90% by volume of each solution is added within 6 minutes. Stirring is maintained for 1 to 2 minutes and then the remaining 10% of the solutions is added within 1 minute and stirring is continued for 2 minutes. The temperature rises from ambient temperature to a final value of 45°–50° C. at the end of the reaction. The polymer precipitates from the mixture 1 minute after the beginning of the addition. The reaction mixture turns yellow at the midpoint of the reaction. At the end of the reaction, the mixture is acidified to a pH close to 2 by means of dilute hydrochloric acid. The polycondensate is washed with water to neutral pH, dried in a vacuum at a temperature of about 50° C. and weighed. 5.1 g of polymer of formula III are recovered (Yield = 83%). ($R = C_6H_5$).

This polymer is a yellow solid, soluble in acetone, chlorinated solvent such as $CHCl_3$, $CH_2Cl_2$, dioxane and tetrahydrofuran. In contrast, it is insoluble in benzene, toluene, methanol, ethanol and water.

The average molecular weight is 24000 (measurement made by gel permeation chromatography in dioxane solution using polystyrene standards).

EXAMPLE 2

Interfacial Polycondensation of Citrochloral Dichloride and L-lysine Benzyl Ester (a) citrochloral (compound of formula d in which $R = CCl_3$)

77 g of citric acid (0.4 mole) and 99.3 g of anhydrous chloral (0.67 mole) are introduced under nitrogen into a three-necked flask fitted with a mechanical stirrer, a condenser and a dropping funnel. The assembly is cooled to 0° C. in an ice bath. 120 ml of concentrated sulfuric acid are added with stirring during about 90 minutes while the temperature is mainteined between 0° and 5° C. by the addition of ice. Stirring is continued for 2 hours at 0° C., then the reaction mixture is brought to ambient temperature and stirred for about 10 hours. At the end of the reaction, the mixture has the appearance of a white paste which is transferred to a beaker containing crushed ince. The white solid is extracted with ethyl acetate and ethyl ether. The organic phase is washed with water until the pH becomes neutral, dried over anhydrous sodium sulfate and evaporated to dryness to give a pinkish viscous oil. This oil is dissolved in 300 ml of chloroform by warming. On cooling, the citrochloral precipitates in the form of a white powder. The precipitate is taken up in 350 ml of boiling ethyl acetate. The gradual addition of petroleum ether to the yellow solution cooled to ambient temperature leads to the precipitation of white crystals, 96.5 g of citrochloral are recovered; yield: 75%. M.p.=163° C. ($CH_3COOC_2H_5$/petroleum ether)

(b) Citrochloral dichloride

It is prepared by the method described in example 1-c. However, the residue obtained on evaporation is dissolved in 20 ml of 1,2-dichloroethane instead of benzene.

9.5 g of the dichloride are obtained from 14 g of diacid in the form of white needles. M.p.=79°–80° C. ($CCL_4$/petroleum ether).

(c) Interfacial polycondensation with L-lysine benzyl ester 8.9 g of the N,N-ditosylate of L-lysine benzyl ester (15.2·10$^{-3}$ mole), 8.71 g of sodium carbonate decahydrate (30.4·10$^{-3}$ mole) and 0.7 g of sodium dodecylsulfate are dissolved with vigorous stirring in a mixture containing 20 cm$^3$ of water, 10 cm$^3$ of dichloromethane, 10 cm$^3$ of 1,2-dichloromethane, 10 cm$^3$ of 1,2-dichloroethane and 30 g of ice.

6 g of citrochloral dichloride (16.7·10$^{-3}$ mole) dissolved in 500 ml of the mixture of the selected chlorinated solvents (V/V-50/50) and 9.58 g of sodium carbonate (33.4·10$^{-3}$ mole) dissolved in 20 cm$^3$ of water are introduced simultaneously. The procedure is similar to that previously described.

At the end of the reaction, the organic phase containing the crude polycondensate is collected. The aqueous phase is acidified and extracted with 50 ml of dichloromethane (twice). The organic solutions are pooled, washed with water and dried over magnesium sulfate. The polycondensate, recovered after evaporation of the organic solvents, is dried in a vacuum at 50° C. 7 g of crude polymer of formula III are recovered (R=CCl$_3$) (Yield: 87%).

The crude polymer of formula III (R=CCl$_3$) has solubilities similar to those of the polymer obtained in example 1; its average molecular weight is 20,000.

The molecular weights of the polymers depend on the conditions of polycondensation, the final temperature and the solvents used: in a benzene/water mixture (50/50-V/V), the polycondensation gives rise to a polymer of 20000 molecular weight, whereas it is only 10000 in a benzene/ice/water mixture (50/20/30) and 14000 in a dichloromethane/dichloroethane/ice/water mixture (25/25/20/30).

EXAMPLE 3

Preparation of the Polymer of Formula IV 1 g of palladized charcoal (10% activated palladium on charcoal) is added to 5 g of the crude copolycondensate obtained in examples 1 or 2 dissolved in 100 cm$^3$ of dimethylformamide (DMF). The mixture is maintained at 60° C. for 24 hours, i.e. until no more hydrogen is taken up.

After the solution has been filtered, the DMF is evaporated under reduced pressure at 50° C. The copolymer is dissolved in 10 cm$^3$ of methanol, then precipitated by about 100 cm$^3$ of diethyl ether. The polymer is obtained in the form of a paste which is dried in an oven under a vacuum at 50° C. overnight. 4.12 g of brownish copolymer of formula IV are obtained as the acid (yield: 84%).

In the case of the polycondensate of example 2, hydrogenolysis is not complete after a reaction time of 24 hours. About 6 to 10 percent of the benzyl ester groups remain bound to lysine (determined by proton NMR); they can be removed by repeating the hydrogenolysis after having introduced into the reaction mixture 0.5 g of fresh palladized charcoal or by hydrolysis for 2 hours at ambient temperature in a DMF/4N HCl mixture (60/40-V/V). At the end of the reaction, the solution is neutralized by the addition of an aqueous solution of 4N NaOH and dialyzed against water in dialysis tubing with a cut-off point of 6000 to 8000, such as that sold by Visking USA under the catalog number 24012. The retentate from which organic solvents, salts and oligomers have been removed is lyophilized to give the sodium salt of the compound of formula IV in the form of a water-soluble brown powder. The IR spectrum (KBr disk) of this salt shows 5 peaks between 1800 and 1500 cm$^{-1}$ corresponding to the characteristic vibrations of an imide carbonyl group (1780 cm$^{-1}$ and 1710 cm$^{-1}$), an amide carboxyl group (1650 cm$^{-1}$ and 1550 cm$^{-1}$) and a carboxylic salt group (1600 cm$^{-1}$). The $^{13}$C NMR spectrum in D$_2$O (external reference: pyridine) shows a double peak for the quaternary carbon of the citric acid unit, one of which at 73.1 ppm corresponds to a carbon included in an imide ring and the other at 75.2 ppm to a carbon bearing free OH and COOH groups. The proportion of imide groups, estimated from the relative surface areas of the two peaks, is about 90%.

The free acid form of the copolymer is generated from its salt by allowing an aqueous solution of the salt to percolate through a cation exchange resin, such as Duolite® C20MB, in the H+ form and isolated by lyophilization. It is a colorless solid, insoluble in water, aromatic and chlorinated solvents, tetrahydrofuran and dioxane but soluble in methanol, dimethylformamide and dimethylsulfoxide.

When the catalytic hydrogenation of the crude polycondensate is carried out in a dioxane/ethanol mixture (50/50-V/V) instead of DMF, cleavage of the benzyl ester groups is complete but some of the acid groups thus liberated are converted into the ethyl ester.

EXAMPLE 4

Preparation of the Copolymer of Formula V by Hydrolysis in Basic Medium 4 g of the product obtained in example 3 are dissolved with stirring in 180 cm$^3$ of 0.7N aqueous NaOH. At the moment when the addition is made the reaction medium turns orange pink. The color disappears after 5 minutes of reaction. The mixture is stirred for 45 minutes. At the end of the reaction, the basic solution is adjusted to 2 g per 100 ml and dialyzed against distilled water in dialysis tubing (WISKASE USA type - cut-off point 6000 to 8000) until the pH becomes neutral (about 2 days). The retentate is then concentrated to 50 cm$^3$ by evaporation under reduced pressure, filtered through a 0.45 μm Millipore membrane, then lyophilized. 3.1 g of the sodium salt of the copolymer of formula V are obtained in the form of a brownish powder which is soluble in water but insoluble in most organic solvents. The average molecular weight is 35,000 (measured by gel permeation chromatography, solvent: 0.15M aqueous solution of KBr; polystyrene sulfonate standards).

The copolymer V in the acid form is obtained by allowing an aqueous solution of its salt to percolate through a Duolite C20MB resin in the H$^+$ form, followed by loyphilization of the eluate.

The copolymer is obtained in the form of a white powder, soluble in water at all pHs, soluble in dimethylformamide, dimethylsulfoxide and methanol but insoluble in chlorinated solvents, tetrahydrofuran, dioxane and acetone.

Titration of the carboxylic acid group by 1M NaOH confirms the presence of two acid groups per repeating unit (mass of a unit=315).

The IR spectrum (KBr disk) shows three peaks between 1800 and 1500 cm$^{-1}$, characteristic of a carboxylic acid group (1740 cm$^{-1}$) and an amide group (1650 and 1550 cm$^{-1}$).

EXAMPLE 5

Preparation of Polymers Starting from Cystamine H$_2$N-(CH$_2$)$_2$-S-S-(CH$_2$)$_2$-NH$_2$ and Citrochloral Dichloride 2.14 g of cystamide hydrochloride (9.5·10$^{-3}$ mole) 5.44 g of sodium carbonate 10H$_2$O for neutralization purposes and 0.4 g of sodium dodecylsulfonate are dissolved in 50 cm$^3$ of a benzene/water mixture (60/40; V/V) with vigorous stirring in a laboratory mixer; 3.74 g of citrochloral dichloride (10.4·10$^{-3}$ mole) dissolved in 30 cm$^3$ of benzene and 5.97 g of sodium carbonate (20.8·10$^{-3}$ mole) dissolved in 20 cm$^3$ of water are then introduced at such a rate that 90% of the solutions are added in 4 minutes, then after one minute of stirring the remaining 10% are added in one minute; the polymer precipitates from the reaction medium in the form of a whitish paste. At the end of the reaction the medium is acidified to pH 2 by the addition of an aqueous solution of HCl; the crude polycondensate is washed with water, then dried in a vacuum at 50° C. 3 g of polymer which contains dioxolane and imide groups are obtained. This product is soluble in strong acids, N-methylpyrrolidone, dimethylsulfoxide and dimethylformamide; it is insoluble in water, alcohols and chlorinated solvents.

Its infrared spectrum is similar to that of the compound of example 2-c in that it shows the peaks characteristic of the cyclic imide group at 1790 and 1710 cm$^{-1}$ and the amide peaks at 1650 and 1550 cm$^{-1}$.

On being treated with a 0.7N aqueous solution of NaOH the imide rings are opened and the polymer of formula V obtained is soluble in water at pH 7.

EXAMPLE 6

Preparation of Polymers Starting from

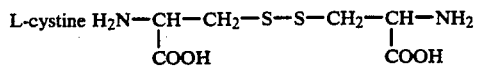

and Citrochloral Dichloride (a) Blockage of the 2 acid groups of L-cystine: ditosylate of L-cystine dibenzyl ester 10 g of L-cystine in 43 ml of benzyl alcohol are dissolved with 17,4 g of para-toluenesulfonic acid in 100 ml of benzene. The reaction mixture is heated at the reflux temperature of the solvent in an extractor of the Dean-Stark type until all the water of reaction has been removed. The mixture is cooled and 50 ml of methanol are added, followed by 500 ml of ethyl ether. 28.8 g of precipitate, melting at 169°-171° C., are thus isolated.

(b) The polycondensation is carried out as described in the preceding example with 10.34 g of the ditosylate of L-cystine dibenzylester, 7.74 g of Na$_2$CO$_3$.10H$_2$O and 0.7 g of sodium dodecylsulfate in 78 cm$^3$ of a C$_6$H$_6$/H$_2$O mixture (66/33; V/V), 5.57 g of citrochloral dichloride dissolved in 52 cm$^3$ of benzene and 8.9 g of Na$_2$CO$_3$.10H$_2$O in 26 cm$^3$ of water.

After working up the reaction mixture, 4.7 g of crude polymer are obtained as a whitish solid soluble in chlorinated solvents (CHCl$_3$, CH$_2$Cl$_2$), dioxane, tetrahydrofuran and acetone and insoluble in alcohols, water and ethyl ether.

Hydrolysis of the benzyl ester groups is carried out by treatment of the polymer with a 33% solution of HBr in acetic acid.

We claim:

1. Polyamides produced by the condensation of diamines with citric acid through the carboxyl groups attached to the carbon atoms in positions 1 and 3.

2. Polyamides according to claim 1 of formula:

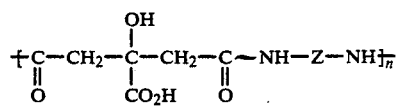

in which n represents an integer lower than 1000, and Z is selected from a C$_2$-C$_{10}$ aliphatic chain, linear or branched, substituted or not by the hydrophilic groups —OH and —COOH, and in which atoms of oxygen or sulfur may be intercalated, or Z is selected from an aryl or alkyraryl chain, and represents the two types of linkage when Z is asymmetric.

3. Polyamides according to claim 2 in which Z represents a C$_2$-C$_8$ aliphatic chain.

4. Polyamides of formula:

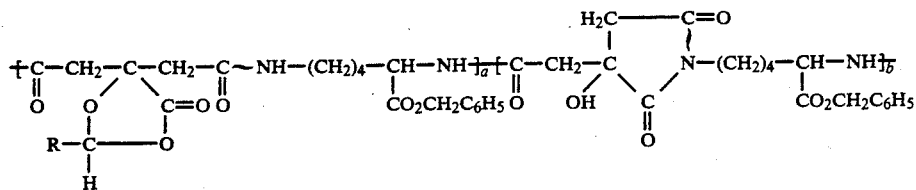

in which R is selected from $C_6H_5$, $CCl_3$, H or $C_1$–$C_4$ alkyl and ~ represents the two types of linkage due to the asymmetric diamine.

5. Polyamides of formula:

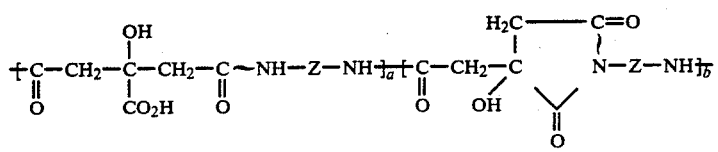

in which Z has the same meanings as in claim 2, a and b are integers and ~ represents the two types of linkage due to the asymmetry of the diamine.

6. Polyamides of formula $A_p$- $B_q$ in which A represents:

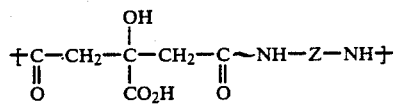

and B represents:

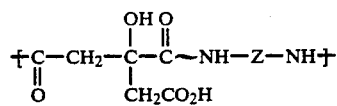

and p and q are integers and ~ represents the two types of linkage due to the asymmetry of the diamine.

7. Process for the preparation of a polyamide as claimed in claim 2, wherein a blocked citric acid having the formula

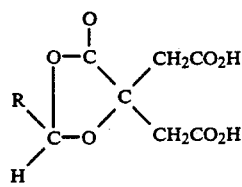

in which R is selected from H, $C_1$–$C_4$ alkyl, $CCl_3$ or $C_6H_5$ is reacted with a diamine of formula $H_2N$—Z'—$NH_2$, in which Z' is Z whose reactive groups of Z are blocked, in polymerization conditions, and the blocking groups are removed by catalytic hydrogenation of hydrolysis.

8. Process for the preparation of a polyamide as claimed in claim 4, wherein a blocked citric acid having the formula

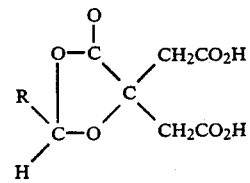

in which R is selected form H, $C_1$–$C_4$ alkyl, $CCl_3$ or $C_6H_5$ is reacted with a diamine of the formula

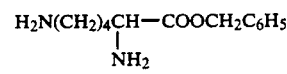

in polymerization conditions.

9. Process for the preparation of a polyamide as claimed in claim 5, wherein a blocked citric acid having the formula

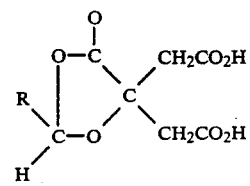

in which R is selected from H, $C_1$–$C_4$ alkyl, $CCl_3$ or $C_6H_5$ is reacted with a diamine of formula $H_2N$—Z'—$NH_2$, in which Z' is Z whose reactive groups are blocked, in polymerization conditions, and the polymer obtained is hydrogenated catalytically.

10. Process according to claim 9 comprising further an acid aqueous hydrolysis after the hydrogenation step.

11. Process for the preparation of a polyamide as claimed in claim 6, wherein a blocked citric acid having the formula

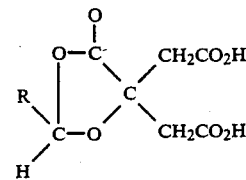

in which R is selected from H, $C_1$-$C_4$ alkyl, $CCl_3$ or $C_6H_5$ is reacted with a diamine of formula $H_2N$—Z'—$NH_2$, in which Z' is Z whose reactive groups are blocked, in polymerization conditions, and the blocked groups of the polymer obtained are removed by hydrolysis in an acidic or basic medium.

12. A controlled-release pharmaceutical composition wherein the carrier is a polyamide as claimed in claim 1.

13. A controlled-release pharmaceutical composition wherein the carrier is a polyamide as claimed in claim 4.

14. A controlled-release pharmaceutical composition wherein the carrier is a polyamide as claimed in claim 5.

15. A controlled-release pharmaceutical composition wherein the carrier is a polyamide as claimed in claim 6.

16. A biodegradable surgical prosthesis or suture or ligature wherein the material is a polyamide as claimed in claim 1.

17. A biodegradable surgical prosthesis or suture or ligature wherein the material is a polyamide as claimed in claim 4.

18. A biodegradable surgical prosthesis or suture or ligature wherein the material is a polyamide as claimed in claim 5.

19. A biodegradable surgical prosthesis or suture or ligature wherein the material is a polyamide as claimed in claim 6.

20. A biodegradable adhesive composition wherein the adhesive material is a polyamide as claimed in claim 1.

21. A biodegradable adhesive composition wherein the adhesive material is a polyamide as claimed in claim 4.

22. A biodegradable adhesive composition wherein the adhesive material is a polyamide as claimed in claim 5.

23. A biodegradable adhesive composition wherein the adhesive material is a polyamide as claimed in claim 6.

* * * * *